United States Patent [19]

Fobare

[11] Patent Number: 5,153,218
[45] Date of Patent: Oct. 6, 1992

[54] N,N',N'-TRISUBSTITUTED-BIS-AMINO-3-METHYLENE-2,4(3H,5H)-FURANDIONE INHIBITORS OF ACYL-COA:CHOLESTEROL-ACYL TRANSFERASE

[75] Inventor: William F. Fobare, Hamilton, N.J.

[73] Assignee: American Home Products Corporation, New York, N.Y.

[21] Appl. No.: 784,202

[22] Filed: Oct. 28, 1991

[51] Int. Cl.$^5$ .............. A61K 31/34; C07D 307/60
[52] U.S. Cl. .................. 514/471; 514/473; 549/313; 549/318
[58] Field of Search ........... 549/313, 318; 514/471, 514/473

[56] References Cited

FOREIGN PATENT DOCUMENTS 2237569  5/1991  United Kingdom .......... 549/313

Primary Examiner—C. Warren Ivy
Assistant Examiner—Ba K. Trinh
Attorney, Agent, or Firm—Richard K. Jackson

[57] ABSTRACT

The compound of the formula:

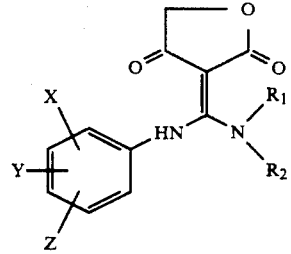

in which X, Y and Z are, independently, hydrogen, halogen, hydroxy, nitro, cyano, carboxyl, trifluoromethyl, phenyl, amino, alkylamino, dialkylamino, alkyl or alkoxy; $R_1$ is alkyl, hydroxyalkyl, alkenyl, cycloalkyl, phenyl, benzyl, phenylethyl or substituted phenyl, benzyl or phenylethyl, alkoxy, halogen, cyano, trifluoromethyl, amino, alkylamino, dialkylamino, nitro, phenyl, benzyl or phenethyl or $R_1$ is thienyl, imidazolyl, thiazolyl, pyridinyl, pyrimidinyl, pyrazinyl or benzamidazolyl; $R_2$ is hydrogen, alkyl, cycloalkyl, phenyl, benzyl or substituted phenyl or benzyl, alkoxy, hologen, cyano, trifluoromethyl amino, nitro, alkylamino or dialkylamino; or a pharmaceutically acceptable salt thereof, are useful as ACAT inhibitors.

18 Claims, No Drawings

N,N',N'-TRISUBSTITUTED-BIS-AMINO-3-METHYLENE-2,4(3H,5H)-FURANDIONE INHIBITORS OF ACYL-COA:CHOLESTEROL-ACYL TRANSFERASE

BACKGROUND OF THE INVENTION

This invention relates to chemical compounds which display inhibition of Acyl-Coenzyme A: Cholesterol Acyltransferase (ACAT). Compounds of this type aid in reducing cholesterol absorption and its effect on atherosclerosis.

Atherosclerosis is the most common form of arteriosclerosis and is characterized by the buildup of phospholipids and esterified cholesterol in large and medium arteries causing them to be inelastic and thus weakened. These inelastic and occluded arteries are the most common cause of ischemic heart disease.

ACAT is an important enzyme for the intracellular esterification of cholesterol. Studies of this enzyme in cultured cells (M. S. Brown, *J. Biol. Chem.* 1980, 617, 458) has shown that increases in ACAT activity represent increases in the presence of cholesterol laden lipoproteins. Regulation of ACAT helps prevent the absorption of cholesterol in the intestinal mucosa, and assists in the reversal of already present atherosclerotic lesions.

DESCRIPTION OF THE INVENTION

In accordance with this invention, there is provided a group of diaminomethylene furandione derivatives of the formula:

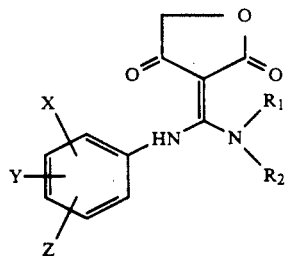

in which
X, Y and Z are, independently, hydroge, halogen, hydroxy, nitro, cyano, carboxyl, trifluoromethyl, phenyl, amino, alkylamino of 1 to 12 carbon atoms, dialkylamino in which each alkyl group has 1 to 12 carbon atoms, alkyl of 1 to 12 carbon atoms or alkoxy of 1 to 12 carbon atoms;

$R_1$ is alkyl of 1 to 18 carbon atoms, hydroxyalkyl of 1 to 18 carbon atoms, alkenyl of 2 to 18 carbon atoms, cycloalkyl of 5 to 8 carbon atoms, phenyl, benzyl, phenylethyl or substituted phenyl, benzyl or phenylethyl where the substituents are alkyl of 1 to 12 carbon atoms, alkoxy of 1 to 12 carbon atoms, halogen, cyano, trifluoromethyl, amino, alkylamino of 1 to 6 carbon atoms, dialkylamino in which each alkyl group has 1 to 6 carbon atoms, nitro, phenyl, benzyl or phenethyl or $R_1$ is thienyl, imidazolyl, thiazolyl, pyridinyl, pyrimidinyl, pyrazinyl or benzamidazolyl;

$R_2$ is hydrogen, alkyl of 1 to 18 carbon atoms, cycloalkyl of 5 to 8 carbon atoms, phenyl, benzyl or substituted phenyl or benzyl in which said substituent is alkyl of 1 to 6 carbon atoms, alkoxy of 1 to 6 carbon atoms, halogen, cyano, trifluoromethyl amino, nitro, alkylamino of 1 to 6 carbon atoms or dialkylamino of 1 to 6 carbon atoms;

or a pharmaceutically acceptable salt thereof.

The halogen substituent referred to above may be chlorine, bromine, fluorine or iodine, fluorine being preferred. The pharmaceutically acceptable salts are derived from known inorganic or organic acids such as hydrochloric, hydrobromic, sulfuric, nitric, phosphoric, methanesulfonic, ethanesulfonic, hydroxyethanesulfonic, toluenesulfonic, naphthalenesulfonic, formic, acetic, propionic, oxalic, succinic, glycollic, lactic, malic, tartaric, citric, ascorbic, maleic, hydroxymaleic, pyruvic, phenylacetic, benzoic, paraaminobenzoic, para-hydroxybenzoic, salicyclic, sulfanilic acids, and the like.

Of these compounds, those preferred on the basis of their in vitro and in vivo potency are:

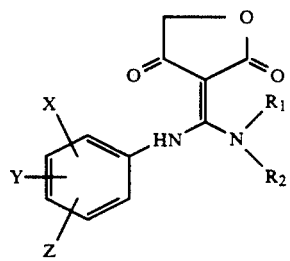

in which
X, Y and Z are, independently, alkyl of 1 to 6 carbon atoms, alkoxy of 1 to 6 carbon atoms, hydroxy, dialkylamino in which each alkyl group has from 1 to 6 carbon atoms or phenyl;

$R_1$ is alkyl of 1 to 8 carbon atoms; and $R_2$ is alkyl of 1 to 8 carbon atoms or alkyl- or alkoxy-substituted benzyl, in which the alkyl and alkoxy substituents contain 1 to 6 carbon atoms;

or a pharmaceutically acceptable salt thereof.

The compounds of this invention are prepared by conversion of tetrahydrofuran-2,4-dione to the corresponding 3-bis(methylthio) methylene derivative with carbon disulfide and methyl iodide in dimethylsulfoxide in the presence of a base such as triethylamine, followed by sequential displacement of the methylthio groups with the desired amines, thusly:

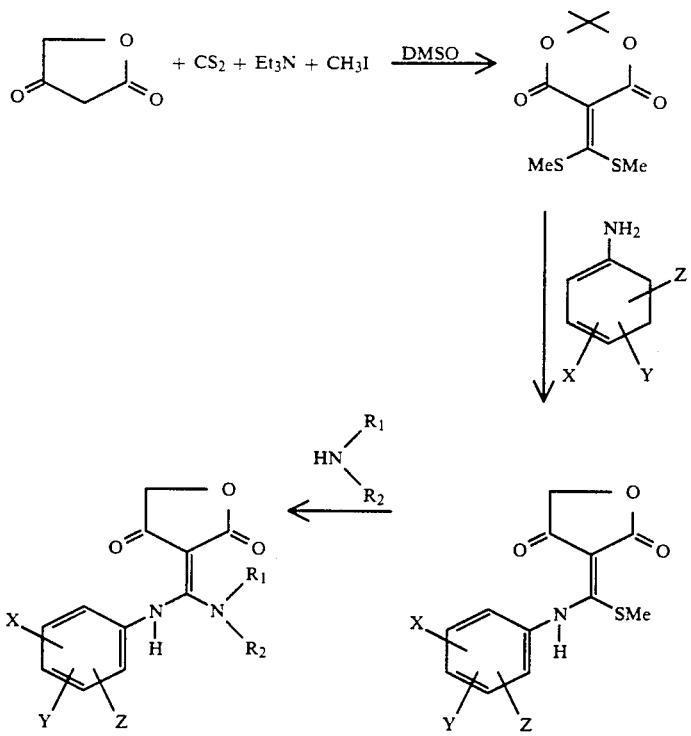

The following examples illustrate without limitation the preparation of representative compounds of this invention.

METHOD A

EXAMPLE 1

3-[[[[4-(1,1-Dimethylethyl)phenyl]methyl]heptylamino][(4-fluorophenyl)amino]methylene]-2,4(3H,5H)-furandione

Procedure 1

To a solution of 37 mL (0.25 mol) 1-heptylamine, 36 mL (0.265 mol) of triethylamine in 300 mL of $CHCl_3$ was added 49.9 mL (0.25 mol) of 4-t-butylbenzoyl chloride dropwise. The reaction mixture was stirred at room temperature for 20 hours then poured into $H_2O$. The layers were separated and the organic layer washed twice with $H_2O$. The $CHCl_3$ layer was dried ($MgSO_4$) and the solvent removed at reduced pressure. The impure compound was used without further purification.

Procedure 2

To a solution of 68.8 g (0.25 mol) of the amide from Procedure 1 in 400 mL of dry toluene was added 105 mL of 70% Red-Al in toluene, dropwise. The reaction mixture stirred at room temperature for 0.5 hours then at reflux for 15 hours. The solution was cooled, quenched with saturated $NH_4Cl$ and the solvent removed at reduced pressure. The residue was taken up in aqueous HCl and the ammonium salt extracted with $CHCl_3$ three times. The combined organic layers were dried ($MgSO_4$) and the solvent removed at reduced pressure. The salt was then crystallized from ether, filtered and washed with ether. The ammonium salt was then added to aqueous NaOH and extracted three times with $Et_2O$. The combined organic layers were dried ($Na_2SO_4$) and the solvent removed at reduced pressure. This amine was used as is without further purification.

Procedure 3

To a solution of 12.0 g (0.12 mol) of tetronic acid in 200 mL of dry DMSO was added 33.45 mL (0.24 mol) of triethylamine and 7.2 mL (0.12 mol) of $CS_2$. The solution was allowed to stir at room temperature for 1 hour. The reaction mixture was cooled to 0° C. and 14.9 mL (0.24 mol) of iodomethane was added dropwise. This solution stirred at 0° C. for an additional 0.5 hours and then at room temperature for 5 hours. The reaction mixture was then poured into 1 liter of ice water and the solid was filtered. Recrystallization from THF-petroleum ether yielded 9.0 g (35%) of a yellow solid. This was used without further purification.

Procedure 4

To a solution of 4.0 g (10.5 mmol) 3-bis(methylthio)-methylene-2,4(3H,5H)-furandione made in Method A, procedure 3, was added 40 mL of t-butanol and 1.85 mL (19.5 mmol) of 4-fluoroaniline. The reaction mixture was allowed to stir at reflux for 4 hours. The mixture was cooled to room temperature and hexane was added to force crystallization. The solid was filtered and washed with hexane. 4.8 g (92%) of a solid was isolated and used as is without further purification.

Procedure 5

To a solution of 0.6 g (2.24 mmol) of the product from Method A, procedure 4, in 10 mL of acetonitrile was added 0.58 g (2.24 mmol) of the amine from Method A, procedure 3, 0.36 g (1.23 mmol) of $HgSO_4$ and 0.31 mL (2.24 mmol) of $Et_3N$. The reaction mixture was allowed to stir at reflux for 3.5 hours. The mixture was cooled to room temperature, diluted with ethyl acetate and filtered through celite. Removal of the solvent at reduced pressure resulted in an oil which was chromatographed on silica gel (1:1 EtOAc-hexanes) to yield 0.97 g (90%) of a solid (m.p. 92°–96° C.).

IR (KBr) 3440, 3230, 2970, 2866, 1742, 1640, 1513, 1445, 1370, 1225, 1161, 1048, 1021 and 834 cm$^{-1}$. $^1$H NMR (400 MHz, CDCl$_3$):δ(9.20 (1H, S, exchangeable), 7.37 (2H, d, J=8.28 Hz), 7.14 (2H, d, J=8.28 Hz), 6.94 (m, 4H), 4.44 (s, 2H), 4.42 (s, 2H), 3.11 (t, 2H, J=7.4 Hz), 1.58 (m, 2H), 1.32 (s, 9H), 1.28–1.21 (m, 8H), 0.86 (t, 3H, J=6.72 Hz).

Elemental analysis for $C_{29}H_{37}FN_2O_3$ : Calc'd: C, 72.47; H, 7.76; N, 5.83. Found: C, 72.71; H, 7.72; N, 5.99.

METHOD B

EXAMPLE 2

3-[(Dihexylamino)[(4-fluorophenyl)amino]methylene]-2,4(3H,5H)furandione

Procedure 1

To a solution of 0.6 g (2.24 mmol) of 3-[[(4-fluorophenyl)amino]methylthiomethylene]-2,4(3H,5H)-furandione in 10 mL of 50:50 acetonitrile-t-butanol was added 1.02 mL (4.4 mmol) of di-N-hexylamine and 0.36 g (1.23 mmol) of mercuric acetate. The reaction mixture was allowed to stir at reflux for 3.5 hours, then cooled to room temperature. The mixture was diluted with a 50:50 mixture of ethyl acetate-hexanes and filtered through celite. The solvent was removed at reduced pressure to give a viscous oil. Column chromatography of the oil on silica gel (3:1 EtOAc-hexanes) yielded 0.68 g (75%) of a solid (m.p. 106°–109° C.).

IR (KBr) 3220, 2938, 2868, 1749, 1712, 1622, 1518, 1482, 1362, 1223, 1161, 1103, 1060, 1020, 838, 791 and 721 cm$^{-1}$. $^1$H NMR (400 MHz, CDCl$_3$):δ9.04 (br s, 1H, exchangeable), 7.10 (m, 4H), 4.39 (s, 2H), 3.25 (t, 4H, J=7.32 Hz), 1.53 (m, 4H), 1.25 (m, 12H), 0.87 (t, 6H, J=6.64 Hz).

Elemental analysis for $C_{23}H_{33}FN_2O_3$: Calc'd: C, 68.29; H, 8.22; N, 6.93. Found: C, 68.32; H, 8.31; N, 6.88.

METHOD C

EXAMPLE 3

3-[[(2,4-Dimethoxyphenyl)amino][[4-(1,1-dimethylethyl)phenyl]heptylamino]methylene]-2,4(3H,5H)-furandione

Procedure 1

To a solution of 4.0 g (19.5 mmol) of 3-bis(methylthio)methylene-2,4(3H,5H)-furandione (Method A, procedure 3) in 30 mL of t-butanol was added 2.98 g (19.5 mmol) of 2,4-dimethoxyaniline. The solution was allowed to reflux for 24 hours. The mixture was cooled to room temperature and hexane was added and the product filtered. Isolated 4.4 g (80%) of a solid which was used without further purification or characterization.

Procedure 2

To a solution of 0.6 g (2.1 mmol) of the product from Method C, procedure 1, in 20 mL of 50:50 acetonitrile-t-butanol was added 0.55 g (2.1 mmol) N-4-t-butylbenzyl-N'-heptylamine (Method A, procedure 3), 0.34 g (1.15 mmol) of mercuric sulfate and 0.29 mL (2.1 mmol) of triethylamine. This was stirred at reflux for 3.5 hours. The solution was cooled, diluted with 50:50 hexanes-ethyl acetate and filtered through celite. The solvent was removed at reduced pressure and column chromatography on silica gel (4:1 ethyl acetate-hexanes) yielded 0.61 g (56%) of a solid (m.p. 130°–133° C.).

IR (KBr) 3360, 2961, 2850, 1742, 1731, 1661, 1608, 1562, 1513, 1440, 1368, 1312, 1279, 1209, 1211, 1179, 1041, 965, 932, 848, 772 and 602 cm$^{-1}$. $^1$H NMR (400 MHz, CDCl$_3$):δ8.4 (br s, 1H, exchangeable), 7.35 (d, 2H, J=8.28 Hz), 7.15 (d, 2H, J=8.28 Hz), 6.83 (d, 1H, J=8.72 Hz), 6.46 (d, 1H, J=2.6 Hz), 6.33 (dd, 1H, J=8.68, 2.56 Hz), 4.41 (s, 2H), 4.37 (s, 2H), 3.79 (s, 3H), 3.77 (s, 3H), 3.16 (t, 2H, J=7.48 Hz), 1.55 (m, 2H), 1.31 (s, 9H), 1.25–1.20 (m, 8H), 0.85 (t, 3H, J=6.76 Hz).

Elemental analysis for $C_{30}H_{42}N_2O_5$: Calc'd: C, 71.23; H, 8.10; N, 5.36. Found: C, 70.88; H, 8.28; N, 5.33.

METHOD D

EXAMPLE 4

3-[[(2,4-Dimethoxyphenyl)amino]((Z)-9-octadecenylamino)methylene]-2,4(3H,5H)-furandione

Procedure 1

To a solution of 0.6 g (2.1 mmol) of the product from Method C, procedure 1 was added 0.86 mL (2.1 mmol) of 80% oleylamine and 30 mL of t-butanol. The reaction mixture was allowed to stir at reflux for 48 hours. The solution was cooled and the solvent removed at reduced pressure. Column chromatography of the residue on silica gel (3:1 hexanes-ethyl acetate) yielded 0.72 g (69%) of a solid (m.p. 39°–41° C.) after recrystallization (ethyl acetate-hexanes).

IR (KBr) 3220, 2915, 2855, 1711, 1645, 1513, 1462, 1314, 1288, 1211, 1162, 1108, 1033, 783 and 699 cm$^{-1}$; $^1$H NMR (400 MHz, CDCl$_3$): δ7.11 (d, 1H, J=8.4 Hz), 6.46 (m, 2H), 5.35 (m, 2H), 4.45 (s, 2H), 3.83 (s, 3H), 3.82 (s, 3H), 2.76 (q, 2H, J=6.32 Hz), 2.00 (br s, 4H), 1.41–1.15 (m, 24H), 0.88 (t, 3H, J=5.8 Hz).

Elemental analysis for $C_{31}H_{48}N_2O_5$: Calc'd: C, 70.42; H, 9.15; N, 5.30. Found: C, 70.24; H, 9.06; N, 5.34.

METHOD E

EXAMPLE 5

3-[[[4-(2,2-Dimethylpropyl)phenylmethyl]heptylamino][(2,4,6-trimethoxyphenyl)amino]methylene]-2,4(3H,5H)-furandione

Procedure 1

The N-4-[(2,2-dimethylpropyl)phenyl]methyl-N'-1-heptylamine was synthesized as in *J. Med. Chem.* 1986, 29, 1131, using 1-aminoheptane and 4-neopentylbenzene as starting materials.

Procedure 2

To a solution of 2.31 g (11.3 mmol) of 3-bis(methyl)thio)methylene-2,4(3H,5H)-furandione was added 2.0 g (11.2 mmol) of 2,4,6-trimethoxyaniline and 50 mL of acetonitrile. The mixture was allowed to stir at reflux for 24 hours then it was cooled to room temperature. A yellow solid was isolated and recrystallized from acetonitrile to yield 1.5 g (39%) of a solid which was used without further purification or characterization.

Procedure 3

To a solution of 0.5 g (1.47 mmol) of the product from Method E, procedure 2 in 20 mL of 50:50 acetonitrile-t-butanol was added 0.41 g (1.47 mmol) of the amine from Method E, procedure 1 and 0.23 g (0.8 mmol) HgSO$_4$ and 0.21 mL (1.47 mmol) of Et$_3$N. The reaction mixture was stirred at reflux for 5 hours. After cooling to room temperature the solution was diluted with ethyl acetate and filtered through celite. The solvent was removed at reduced pressure and column chromatography of the residue on silica gel (3:2 ethyl acetate-hexanes) yielded 0.67 g (81%) of a solid (m.p. 62°-62° C.) homogeneous by spectroscopic criteria.

IR (KBr) 3240, 2945, 2848, 1736, 1642, 1601, 1506, 1435, 1368, 1222, 1208, 1158, 1132, 1048, 1009, 811 cm$^{-1}$. $^1$H NMR (400 MHz, CDCl$_3$): δ8.13 (br s, 1H, exchangeable), 7.13 (d, 2H, J=8.04 Hz), 7.06 (d, 2H, J=8.04 Hz), 6.13 (s, 2H), 4.38 (s, 2H), 4.32 (s, 2H), 3.83 (s, 3H), 3.76 (s, 6H), 3.19 (t, 2H, J=7.84 Hz), 2.45 (s, 2H), 1.44 (m, 2H), 1.25-1.09 (m, 8H), 0.87 (s, 9H), 0.84 (t, 3H, J=6.96 Hz).

Elemental analysis for C$_{33}$H$_{46}$N$_2$O$_6$: Calc'd: C, 69.94; H, 8.18; N, 4.94. Found: C, 69.91; H, 8.08; N, 5.25.

METHOD F

EXAMPLE 6

3-[[(2,4-Dimethoxyphenyl)amino][(heptyl)][[4-(3-methylbutoxy)phenyl]methyl]amino]methylene]-2,4(3H,5H)-furandione

Procedure 1

To a solution of 10.0 g (60 mmol) of ethyl 4-hydroxybutyrate in 200 mL of dimethylformamide was added 8.3 g (60 mmol) of anhydrous potassium carbonate and 7.2 mL (60 mmol) of 2-methyl-4-bromobutane. Then 100 mL of dry DMSO was added and the mixture stirred at room temperature for 12 days. The mixture was poured into H$_2$O and extracted twice with diethyl ether. The combined diethyl ether layers were washed twice with water, dried (MgSO$_4$) and the solvent was removed at reduced pressure. The residue was taken up in 150 mL of MeOH and 130 mL of 1N NaOH was added. The solution stirred at room temperature for 24 hours. The solution was poured into water and extracted with diethyl ether. The aqueous layer was made basic (NaOH) and extracted 3 times with ethyl acetate. The combined ethyl acetate layers were washed with saturated NaCl, dried (MgSO$_4$) and the solvent was removed at reduced pressure. The solid obtained was then recrystallized from ethyl acetate to yield 10.2 g (82%) of a white solid which was used without further characterization or purification.

Procedure 2

To a solution of 10.2 g (49 mmol) of the acid from Method F, procedure 1 in 250 mL of CHCl$_3$ was added 6.8 mL (78 mmol) of oxalyl chloride. This stirred at room temperature for 1 hour then at reflux for 14 hours. The solution was cooled to room temperature then poured into H$_2$O and the CHCl$_3$ layer separated, dried (MgSO$_4$) and the solvent removed at reduced pressure. This material was mixed with 150 mL of CHCl$_3$, 6.8 mL (49 mmol) of Et$_3$N, cooled to 0° C. and 7.26 mL (49 mmol) of 1-aminoheptane was added. After 2 hours at 0° C. and 2 hours at room temperature the solution was washed twice with H$_2$O, dried (MgSO$_4$) and the solvent removed at reduced pressure. The solid obtained was used without further purification or characterization.

Procedure 3

To a solution of the solid from Method F, procedure 2 in 200 mL of toluene was added 21.6 mL of 3.4M Red-Al over a 25 min period. The solution was allowed to stir at room temperature for 1 hour then at reflux for 12 hours. The toluene was removed at reduced pressure and the residue poured into 2N HCl. The solution was extracted with CHCl$_3$ which was dried (MgSO$_4$) and the solvent removed at reduced pressure. This hydrochloride salt was triturated with ether then added to aqueous NaOH and the free amine was extracted with diethyl ether. The combined diethyl ether layers were dried (Na$_2$SO$_4$) and the solvents removed at reduced pressure. The oil obtained was used without further purification or characterization.

Procedure 4

To a solution of 0.6 g (1.94 mmol) of the compound obtained in Method C, procedure 1 in 20 mL of 50:50 acetonitrile-t-butanol was added 0.54 g (1.94 mmol) of the amine from Method F, procedure 3, 0.34 g HgSO$_4$ (1.06 mmol) and 0.27 mL of triethylamine. The mixture was allowed to stir at reflux for 8 hours. The mixture was cooled to room temperature, diluted with ethyl acetate, filtered through celite then the solvents were removed at reduced pressure. Column chromatography of the residue on silica gel (1:1 ethyl acetate-hexanes) yielded 0.58 g (54%) of a solid (m.p. 56°-60° C.) homogeneous by spectroscopic considerations.

IR (KBr) 3245, 2980, 2952, 2896, 1752, 1643, 1578, 1523, 1448, 1318, 1245, 1218, 1169, 1051 and 833 cm$^{-1}$. $^1$H NMR (400 MHz, CDCl$_3$): δ8.55 (br s, 1H, exchangeable), 7.14 (d, 2H, J=8.94 Hz), 6.87 (m, 3H), 6.47 (d, 1H, J=2.36 Hz), 6.36 (dd, 1H, J=8.68, 2.44 Hz), 4.41 (s, 2H), 4.35 (s, 2H), 3.97 (t, 2H, J=6.64 Hz), 3.80 (s, 3H), 3.79 (s, 3H), 3.11 (t, 2H, J=7.40 Hz), 1.83 (m, 1H), 1.67 (q, 2H, J=6.64 Hz), 1.52 (m, 2H), 1.25-1.12 (m, 8H), 0.96 (d, 6H, J=6.56 Hz), 0.85 (t, 3H, J=6.8 Hz).

Elemental analysis for C$_{32}$H$_{44}$N$_2$O$_6$: Calc'd: C, 69.54; H, 8.02; N, 5.07. Found: C, 69.34; H, 8.30; N, 4.98.

METHOD G

EXAMPLE 7

3-[[(2,4-Dimethoxyphenyl]amino][[[4-(2,2-dimethylpropyl)phenyl]methyl](1-methylhexyl)-amino]methylene]2,4(3H,5H)-furandione

Procedure 1

N-4-(2,2-dimethylpropyl)benzyl-N'-methylhexylamine was synthesized and used in the same manner as in Method E, procedure 1 except 2-aminoheptane was used with 2,2-dimethylpropylbenzene.

Procedure 2

To a solution of 0.5 g (1.6 mmol) of the compound isolated in Method C, procedure 1, in 20 mL acetonitrile was added 0.45 g (1.6 mmol) of the amine isolated in Method G, procedure 1, 0.22 mL (1.6 mmol) of Et$_3$N and 0.26 g (0.9 mmol) of HgSO$_4$. The reaction mixture was allowed to reflux for 12 hours. The mixture was cooled to room temperature, diluted with ethyl acetate, filtered through celite then the solvents were removed under reduced pressure. Column chromatography of the residue on silica gel (1:1 ethyl acetate-hexanes) yielded 0.41 g (49%) of a solid (m.p. 140°-142° C.) homogeneous by spectroscopic considerations.

IR (KBr) 3180, 2929, 2835, 1718, 1608, 1549, 1501, 1456, 1302, 1276, 1227, 1198, 1157, 1019, 998 and 818 cm$^{-1}$. $^1$H NMR (400 Mhz, CDCl$_3$): δ7.88 (br s, 1H, exchangeable), 7.04 (s, 4H), 6.85 (d, 1H, J=8.72 Hz), 6.43 (d, 1H, J=2.48 Hz), 6.34 (dd, 1H, J=2.48, 8.72 Hz), 4.55 (ABq, 2H, J$_{AB}$=16.6 Hz, Δν$_{AB}$=7.01 Hz), 4.28 (ABq, 2H, J=153.6 Hz, Δν$_{AB}$=7.37 Hz), 4.05 (m, 1H), 3.78 (s, 3H), 3.71 (s, 3H), 2.45 (s, 2H), 1.69–1.18 (m, 11H), 0.89–0.84 (m, 12H).

Elemental analysis for $C_{32}H_{44}N_2O_5$: Calc'd: C, 71.61; H, 8.26; N, 5.22. Found: C, 71.90; H, 8.27; N, 5.22.

METHOD H

EXAMPLE 8

3-[[[3,5-(Bis(1,1-dimethylethyl)-4-hydroxyphenyl]amino][[[4-(2,2-dimethylpropyl)phenyl]-methyl](1-methylhexyl)amino]methylene]2,4(3H,5H)-furandione Procedure 1

To a solution of 2.85 g (14 mmol) 3-bis(methylthio)-methylene-2,4(3H,5H)furandione in 30 mL of acetonitrile was added 4.0 g (14.5 mmol) of the 3,5-di-t-butyl-4-hydroxyaniline hydrochloride. The solution was degassed with argon and 2.0 mL (14.5 mmol) of triethylamine was added. The solution stirred at room temperature for 24 hours. The acetonitrile was removed at room temperature and the residue was taken up in ethyl acetate and washed 3 times with $H_2O$. The ethyl acetate layer was dried ($MgSO_4$) and the solvent removed at reduced pressure. Column chromatography of the residue on silica gel (4:1 to 2:1 hexanes-ethyl acetate) yielded 3.4 g (62%) of a solid which was used without further purification or characterization.

Procedure 2

To a solution of 0.8 g (2.0 mmol) of the product from Method H, procedure 1 in 20 mL of acetonitrile was added 0.56 g (2.0 mmol) of the amine synthesized in Method G, procedure 1, 0.28 mL (2.0 mmol) of triethylamine and 0.32 g (1.1 mmol) of $HgSO_4$. The reaction mixture was allowed to stir at reflux for 18 hours. This mixture was cooled to room temperature, diluted with ethyl acetate and filtered through celite. The solvent was removed at reduced pressure and column chromatography of the residue of the residue on silica gel (3:1 to 1:2 hexanes-ethyl acetate) yielded 0.88 g (73%) of a solid (m.p. 210°–212° C.) which was homogeneous by spectroscopic considerations.

IR (KBr) 3648, 3210, 2955, 2870, 1735, 1716, 1636, 1575, 1503, 1436, 1413, 1366, 1319, 1213, 1160, 1038, 1021 and 772 $cm^{-1}$. $^1H$ NMR (400 MHz, $CDCl_3$): $\delta 8.89$ (br s, 1H, exchangeable), 7.02 (d, 2H, J=8.08 Hz), 6.91 (d, 2H, J=8.08 Hz), 6.74 (s, 2H), 5.28 (s, 1H), 4.37 (ABq, 2H, $J_{AB}$=15.49 Hz, $\Delta v_{AB}$=6.17 Hz), 4.26–4.11 (m, 3H), 2.45 (s, 2H), 1.73 (m, 2H), 1.44–1.25 (m, 27H), 0.88 (m, 12H).

Elemental analysis for $C_{38}H_{56}N_2O_4$: Calc'd: C, 75.46; H, 9.33; N, 4.63. Found: C, 75.38; H, 9.65; N, 4.62.

EXAMPLE 9

3-[(Dihexylamino)[(2,4-dimethoxyphenyl)amino]methylene]-2,4(3H,5H)-furandione

This compound was synthesized using the procedure as in Method B except 2,4-dimethoxyaniline was used. This yielded (73%) a solid (m.p. 96°–98° C.) which was homogeneous by spectroscopic criteria.

Elemental analysis for $C_{25}H_{38}N_2O_5$: Calc'd: C, 67.24; H, 8.58; N, 6.27. Found: C, 67.52; H, 8.87; N, 6.13.

METHOD I

EXAMPLE 10

3-[[(4-Fluorophenyl)amino]((Z)-9-octadecenylamino)-methylene]2,4(3H,5H)-furandione To a solution of 0.6 g (2.24 mmol) of the product from Method A, procedure 4 in 15 mL of t-butyl alcohol was added 0.92 mL (2.8 mmol) of 80% oleyl amine. The reaction mixture was allowed to stir at reflux for 16 hours. The mixture was cooled and the solvent was removed at reduced pressure. Column chromatography of the residue on silica gel (4:1 hexanes-ethyl acetate) yielded 0.55 g of an oil, homogeneous by spectroscopic considerations.

IR ($CHCl_3$) 3230, 3005, 2935, 2863, 1711, 1648, 1512, 1465, 1451, 1336, 1232, 1109, 1033 and 837 $cm^{-1}$. $^1H$ NMR (400 MHz, $CDCl_3$) $\delta 7.21$ (dd, 2H, J=2.4, 8.24 Hz), 7.11 (t, 2H, J=8.24 Hz), 5.31 (m, 2H), 4.48 (s, 2H), 2.75 (q, 2H, J=6.88 Hz), 1.98 (m, 4H), 1.45 (m, 2H), 1.29–1.17 (m, 22H), 0.88 (t, 3H, J=6.48 Hz).

Elemental analysis for $C_{29}H_{43}FN_2O_3$: Calc'd: C, 71.57; H, 8.91; N, 5.76. Found: C, 71.39; H, 9.01; N, 5.90.

EXAMPLE 11

3-[[(2,4-Dimethoxyphenyl)amino][(2-phenylethyl)(phenylmethyl)amino]methylene]-2,4(3H,5H)-furandione This compound was synthesized using the same procedure as in Method C, procedure 2 except N-benzyl-N'-phenylethylamine was used. This yielded a solid (m.p. 79°–84° C.) which was homogeneous by spectroscopic criteria.

Elemental analysis for $C_{28}H_{28}N_2O_5 \cdot 0.25H_2O$: Calc'd: C, 70.49; H, 6.02; N, 5.86. Found: C, 70.50; H, 5.85; N, 5.86.

EXAMPLE 12

3-[([1,1'-Biphenyl]-4-ylamino)(dihexylamino)methylene]-2,4(3H,5H)-furandione

This compound was synthesized using the same procedure as in Method B except 4-aminobiphenyl was used. This yielded a solid (m.p. 138°–140° C.) which was homogeneous by spectroscopic criteria.

Elemental analysis for $C_{29}H_{38}N_2O_3$: Calc'd: C, 75.29; H, 8.28; N, 6.06. Found: C, 75.45; H, 8.22; N, 6.07.

EXAMPLE 13

3-[([1,1'-Biphenyl]-4-ylamino)[[[4-(1,1-dimethylethyl)-phenyl]methyl]heptylamino]methylene]-2,4(3H,5H)-furandione This compound was synthesized using the same procedure as in Method C, except 4-aminobiphenyl was used. This yielded a solid (m.p. 190°–192° C.) which was homogeneous by spectroscopic criteria.

Elemental analysis for $C_{35}H_{42}N_2O_3$: Calc'd: C, 78.03; H, 7.86; N, 5.20. Found: C, 77.93; H, 7.90; N, 5.18.

EXAMPLE 14

3-[[(2,4-Difluorophenyl)amino][[[4-(1,1-dimethylethyl)-phenyl]methyl]heptylamino]methylene]-2,4(3H,5H)-furandione This compound was synthesized using the same procedure as in Method C, except 2,4-difluoroaniline was used. This yielded a solid (m.p. 89°–92° C.) homogeneous by spectroscopic criteria.

Elemental analysis for $C_{29}H_{36}F_2N_2O_3$: Calc'd: C, 69.86; H, 7.28; N, 5.62. Found: C, 69.77; H, 7.28; N, 5.70.

EXAMPLE 15

3-[[[[4-(1,1-Dimethylethyl)phenyl]methyl]heptylamino][(2,4,6-trimethylphenyl)amino]methylene]-2,4(3H,5H)-furandione This compound was synthesized using the same procedure as in Method C except 2,4,6-trimethylaniline was used. This yielded a solid (m.p. 141°–143° C.) homogeneous by spectroscopic criteria.

Elemental analysis for $C_{32}H_{44}N_2O_3$: Calc'd: C, 76.15; H, 8.79; N, 5.55. Found: C, 76.19; H, 8.81; N, 5.59.

EXAMPLE 16

3-[[Heptyl[(4-hexylphenyl)methyl]amino][[4-(trifluoromethyl)phenyl]amino]methylene]-2,4(3H,5H)-furandione This compound was synthesized using the same procedure in Method C except 4-aminobenzotrifluoride and 4-hexyl benzoyl chloride were used. This yielded a solid (m.p. 94°–98° C.) homogeneous by spectroscopic criteria.

Elemental analysis for $C_{32}H_{41}F_3N_2O_3$: Calc'd: C, 68.76; H, 7.40; N, 5.01. Found: C, 68.40; H, 7.22; N, 4.96.

EXAMPLE 17

3-[[(4-Chlorophenyl)amino][[[4-(1,1-dimethylethyl)phenyl]methyl]heptylamino]methylene]-2,4(3H,5H)-furandione This compound was synthesized using the same procedure in Method C except 4-chloroaniline was used. This yielded a solid (m.p. 101°–104° C.) homogeneous by spectroscopic criteria.

Elemental analysis for $C_{29}H_{37}ClN_2O_3$: Calc'd: C, 70.07; H, 7.50; N, 5.63. Found: C, 70.09; H, 7.43; N, 5.48.

EXAMPLE 18

3-[[[[4-(1,1-Dimethylethyl)phenyl]methyl]((Z)-9-octadecenyl)amino][(4-fluorophenyl)amino]methylene]-2,4(3H,5H)-furandione This compound was synthesized using the procedure in Method C except oleyl amine was used in place of 1-aminoheptane. This yielded a sticky solid which was characterized by NMR and IR.

IR (CHCl$_3$) 3250, 3010, 2932, 2858, 1748, 1655, 1568, 1511, 1440, 1412, 1235, 1052, 1020 and 837 cm$^{-1}$. $^1$H NMR (400 MHz, CDCl$_3$): δ9.21 (br s, 1H), 7.37 (d, 2H, J=8.32 Hz), 7.14 (d, 2H, J=8.32 Hz), 6.95 (m, 4H), 5.34 (m, 2H), 4.44 (s, 2H), 4.42 (s, 2H), 3.11 (t, 2H, J=7.32 Hz), 2.01 (m, 4H), 1.57 (m, 2H), 1.32–1.21 (m, 31H), 0.87 (t, 3H, J=6.68 Hz).

EXAMPLE 19

3-[[[4-(Dimethylamino)-2,6-dimethylphenyl]amino][[4-(1,1-dimethylethyl)phenyl]heptylamino]methylene]-2,4(3H,5H)-furandione This compound was synthesized using the procedure in Method C except 4-dimethylamino-2,6-dimethylaniline was used. This yielded a solid (m.p. 144°–147° C.) homogeneous by spectroscopic criteria.

Elemental analysis for $C_{33}H_{47}N_3O_3$: Calc'd: C, 74.26; H, 8.87; N, 7.87. Found: C, 74.39; H, 9.00; N, 7.96.

EXAMPLE 20

3-[[(2,4-Dimethoxyphenyl)amino][[[4-(1,1-dimethylethyl)phenyl]methyl](1-methylhexyl)amino]methylene]-2,4(3H,5H)-furandione This compound was synthesized using the procedure in Method C except 2-aminoheptane was used in place of 1-aminoheptane. This yielded a solid (m.p. 115°–117° C.) homogeneous by spectroscopic criteria.

Elemental analysis for $C_{31}H_{42}N_2O_5$: Calc'd: C, 71.24; H, 8.10; N, 5.36. Found: C, 71.13; H, 8.08; N, 5.28.

EXAMPLE 21

3-[[(2,4-Dimethoxyphenyl)amino][[[4-(3-methylbutoxy)phenyl]methyl](1-methylhexyl)amino]methylene]-2,4(3H,5H)-furandione This compound was synthesized using the procedure in Method F except 2-aminoheptane was used in place of 1-aminoheptane. This yielded a solid (m.p. 125°–127° C.) homogeneous by spectroscopic criteria.

Elemental analysis for $C_{32}H_{44}N_2O_6$: Calc'd: C, 69.54; H, 8.02; N, 5.07. Found: C, 69.32; H, 7.86; N, 4.88.

EXAMPLE 22

3-[[[3,5-Bis(1,1-dimethylethyl)-4-hydroxyphenyl]amino][[[4-(2,2-dimethylpropyl)phenyl]methyl](1-methylheptyl)amino]methylene]-2,4(3H,5H)-furandione This compound was synthesized using the procedure in Method H except 2-aminooctane was used in place of 2-aminoheptane. This yielded a solid (m.p. 158°–160° C.) homogeneous by spectroscopic criteria.

Elemental analysis for $C_{39}H_{58}N_2O_4$: Calc'd: C, 75.69; H, 9.45; N, 4.53. Found: C, 75.58; H, 9.12; N, 4.47.

EXAMPLE 23

3-[[[3,5-Bis(1,1-dimethylethyl)-4-hydroxyphenyl]amino]hexyl[[4-(2-methylpropyl)phenyl]methyl]amino]methylene]-2,4(3H,5H)-furandione This compound was synthesized according to the procedure in Method H except that isobutylbenzene and 1-aminohexane were used for neopentylbenzene and 2-aminoheptane. This yielded a solid (m.p. 188°–190° C.) homogeneous by spectroscopic criteria.

Elemental analysis for $C_{36}H_{52}N_2O_4$: Calc'd: C, 74.96; H, 9.09; N, 4.86. Found: C, 74.99; H, 9.10; N, 4.89.

The ability of the compounds of this invention to inhibit acyl-coenzyme A: cholesterol acyltransferase was established in vitro by initially showing that they inhibited intracellular cholesterol esterification by subjecting them to the standard experimental test procedure of Ross et al., J. Biol. Chem. 259 815 (1984).

Representative compounds were further tested in vivo to establish the percent inhibition of cholesterol absorption. In this study, normal rats were dosed (oral gavage) with $^{14}$C-cholesterol plus the test compound. Blood samples taken at six hours and/or intermittently up to twenty-four hours were analyzed and the percent inhibition of cholesterol absorption was calculated.

In addition, representative compounds were studied in vivo in cholesterol-cholic acid fed rats to determine the percent decrease of cholesterol in their plasma. This study involves rats which are, prior to testing, trained for one week to eat over a four hour time period each day. Upon initiation of the experiment, the rats diet is supplemented with 1.0 percent cholesterol and 0.25 percent cholic acid. The rats are dosed with the test compound by oral gavage just prior to and just following the four hour feeding period. This is repeated for four days. On the fifth day, the rats are sacrificed and the total plasma cholesterol content is determined. The percent decrease in elevated plasma cholesterol levels is calculated in comparison with normal-fed controls.

The results of these studies are as follows:

TABLE 1

| Example | In Vitro $IC_{50}$ Inhibition (Conc., mM) | $IC_{50}$ (mM) |
|---|---|---|
| 1 | 96 (50) | 6 |
| 2 | 57 (50) | — |
| 3 | 90 (50) | 4 |
| 4 | 63 (50) | — |
| 5 | 67 (25) | 11 |
| 6 | 99 (25) | 0.4 |
| 7 | 98 (25) | 0.92 |
| 8 | 99 (25) | 0.19 |
| 9 | 87 (50) | 25 |
| 10 | 61 (50) | >30 |
| 11 | 72 (50) | >30 |
| 12 | 90 (50) | 27 |
| 13 | 91 (50) | 12 |
| 14 | 39 (25) | — |
| 15 | 73 (25) | — |
| 16 | 56 (25) | — |
| 17 | 84 (25) | 24 |
| 18 | 44 (25) | — |
| 19 | 77 (25) | 9.5 |
| 20 | 94 (25) | 1.5 |
| 21 | 97 (25) | 4.9 |
| 22 | 97 (25) | 0.07 |
| 23 | 88 (25) | — |

TABLE 2

| Example | In Vivo Testing Dose mg/kg | 14C-Cholesterol Absorption in Normal Rats % Inhibition of Absorption |
|---|---|---|
| 1 | 200 | −74 |
| 4 | 200 | −14 |
| 7 | 20 | −62 |
| 8 | 20 | −72 |

TABLE 3

In Vivo Testing Cholesterol-Cholic Acid Fed Rats

| Example | Dose mg/kg | % Decrease in Plasma Cholesterol |
|---|---|---|
| 7 | 40 | −26 |
| 8 | 20 | −71 |
| 21 | 20 | −23 |
| 22 | 20 | −80 |

From these data, the ability of the compounds to inhibit ACAT is clearly established. Hence, the compounds of this invention are useful in the treatment of those disease states which are amenable to treatment by reduction of the rate of cholesterol esterification, the rate of accumulation and deposits of cholesteryl esters on arterial walls and the rate of formation of atheromatous lesions. As such, the anti-atherosclerotic agents of this invention may be administered to a mammal in need of intracellular cholesteryl ester concentration reduction orally or parenterally in an amount sufficient to inhibit ACAT catalysis of cholesterol esterification.

The compounds of this invention may be administered by themselves or in combination with pharmaceutically acceptable liquid or solid carriers. Oral administration in conventional formulations as tablets, capsules, powders, or suspensions is preferred.

A solid carrier can include one or more substances which may also act as flavoring agents, lubricants, solubilisers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both of pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g., glycols) and their derivatives, and oils (e.g. fractionated coconut oil and arachis oil). For parenteral administration, the carrier can also be an oil ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular intraperitoneal or subcutaneous injection. Sterile solutions can also be administered intravenously. When the compound is orally active, it can be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific hypercholesterolemic/atherosclerotic condition must be subjectively determined by the attending physician. The variables involved include the extent of the disease state, size, age and response pattern of the patient.

What is claimed is:

1. A compound of the formula:

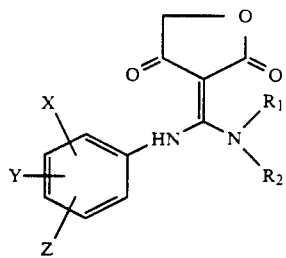

in which
X, Y and Z are, independently, hydrogen, halogen, hydroxy, nitro, cyano, carboxyl, trifluoromethyl, phenyl, amino, alkylamino of 1 to 12 carbon atoms, dialkylamino in which each alkyl group has 1 to 12 carbon atoms, alkyl of 1 to 12 carbon atoms or alkoxy of 1 to 12 carbon atoms;

$R_1$ is alkyl of 1 to 18 carbon atoms, hydroxyalkyl of 1 to 18 carbon atoms, alkenyl of 2 to 18 carbon atoms, cycloalkyl of 5 to 8 carbon atoms, phenyl, benzyl, phenylethyl or substituted phenyl, benzyl or phenylethyl where the substituents are alkyl of 1 to 12 carbon atoms, alkoxy of 1 to 12 carbon atoms, halogen, cyano, trifluoromethyl, amino, alkylamino of 1 to 6 carbon atoms, dialkylamino in which each alkyl group has 1 to 6 carbon atoms, nitro, phenyl, benzyl or phenethyl;

$R_2$ is hydrogen, alkyl of 1 to 18 carbon atoms, cycloalkyl of 5 to 8 carbon atoms, phenyl, benzyl or substituted phenyl or benzyl in which said substituent is alkyl of 1 to 6 carbon atoms, alkoxy of 1 to 6 carbon atoms, halogen, cyano, trifluoromethyl amino, nitro, alkylamino of 1 to 6 carbon atoms or dialkylamino of 1 to 6 carbon atoms;

or a pharmaceutically acceptable salt thereof.

2. A compound of claim 1 of the formula:

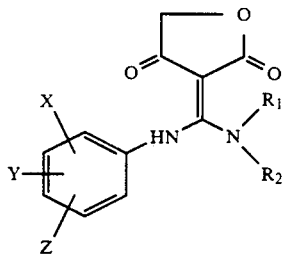

in which
X, Y and Z are, independently, alkyl of 1 to 6 carbon atoms, alkoxy of 1 to 6 carbon atoms, hydroxy, dialkylamino in which each alkyl group has from 1 to 6 carbon atoms or phenyl;

$R_1$ is alkyl of 1 to 8 carbon atoms;
and
$R_2$ is alkyl of 1 to 8 carbon atoms or alkyl- or alkoxy-substituted benzyl, in which the alkyl and alkoxy substituents contain 1 to 6 carbon atoms;

or a pharmaceutically acceptable salt thereof.

3. A compound of claim 1 which is 3-[[[[4-(1,1-dimethylethyl)phenyl]methyl]heptylamino][(4-fluorophenyl)amino]methylene]-2,4(3H,5H)-furandione, or a pharmaceutically acceptable salt thereof.

4. A compound of claim 1 which is 3-[[(2,4-dimethoxyphenyl)amino][[4-(1,1-dimethylethyl)phenyl]heptylamino]methylene]-2,4(3H,5H)-furandione, or a pharmaceutically acceptable salt thereof.

5. A compound of claim 1 which is 3-[[(2,4-dimethoxyphenyl)amino][(heptyl)[[4-(3-methylbutoxy)phenyl]methyl]amino]methylene]-2,4(3H,5H)-furandione, or a pharmaceutically acceptable salt thereof.

6. A compound of claim 1 which is 3-[[(2,4-dimethoxyphenyl]amino][[[4-(2,2-dimethylpropyl)phenyl]methyl](1-methylhexyl)amino]methylene]-2,4(3H,5H)-furandione, or a pharmaceutically acceptable salt thereof.

7. A compound of claim 1 which is 3-[[[3,5-(bis(1,1-dimethylethyl)-4-hydroxyphenyl]amino][[4-(2,2-dimethylpropyl)phenyl]-methyl](1-methylhexyl)amino]methylene]-2,4(3H,5H)-furandione, or a pharmaceutically acceptable salt thereof.

8. A compound of claim 1 which is 3-[(dihexylamino)[(2,4-dimethoxyphenyl)amino]methylene]-2,4(3H,5H)-furandione, or a pharmaceutically acceptable salt thereof.

9. A compound of claim 1 which is 3-[([1,1'-biphenyl]-4-ylamino)(dihexylamino)methylene]-2,4(3H,5H)-furandione, or a pharmaceutically acceptable salt thereof.

10. A compound of claim 1 which is 3-[([1,1'-biphenyl]-4-ylamino)[[[4-(1,1-dimethylethyl)phenyl]methyl]heptylamino]methylene]-2,4(3H,5H)-furandione, or a pharmaceutically acceptable salt thereof.

11. A compound of claim 1 which is 3-[[(4-chlorophenyl)amino][[[4-(1,1-dimethylethyl)phenyl]methyl]heptylamino]methylene]-2,4(3H,5H)-furandione, or a pharmaceutically acceptable salt thereof.

12. A compound of claim 1 which is 3-[[(2,4-dimethoxyphenyl)amino][[[4-(1,1-dimethylethyl)phenyl]methyl](1-methylhexyl)amino]methylene]-2,4(3H,5H)-furandione, or a pharmaceutically acceptable salt thereof.

13. A compound of claim 1 which is 3-[[(2,4-dimethoxyphenyl)amino][[[4-(3-methylbutoxy)phenyl]methyl](1-methylhexyl)amino]methylene]-2,4(3H,5H)-furandione, or a pharmaceutically acceptable salt thereof.

14. A compound of claim 1 which is 3-[[[3,5-bis(1,1-dimethylethyl)-4-hydroxyphenyl]amino][[[4-(2,2-dimethylpropyl)phenyl]methyl](1-methylheptyl)amino]methylene]-2,4(3H,5H)-furandione, or a pharmaceutically acceptable salt thereof.

15. A compound of claim 1 which is 3-[[[3,5-bis(1,1-dimethylethyl)-4-hydroxyphenyl]amino]hexyl[[4-(2-methylpropyl)phenyl]methyl]amino]methylene]-2,4(3H,5H)-furandione, or a pharmaceutically acceptable salt thereof.

16. A compound of claim 1 which is:
3-[(dihexylamino)[(4-fluorophenyl)amino]methylene]-2,4(3H,5H)-furandione;
3-[[(2,4-dimethoxyphenyl)amino]((Z)-9-octadecenylamino)methylene]-2,4(3H,5H)-furandione;
3-[[[4-(2,2-dimethylpropyl)phenylmethyl]heptylamino][(2,4,6-trimethoxyphenyl)amino]methylene]-2,4(3H,5H)-furandione;
3-[[(4-fluorophenyl)amino]((Z)-9-octadecenylamino)methylene]-2,4(3H,5H)furandione;
3-[[(2,4-dimethoxyphenyl)amino][(2-phenylethyl)(phenylmethyl)amino]methylene]-2,4(3H,5H)-furandione;

3-[[(2,4-difluorophenyl)amino][[[4-(1,1-dimethylethyl)-phenyl]methyl]heptylamino]methylene]-2,4(3H,5H)-furandione;

3-[[[[4-(1,1-dimethylethyl)phenyl]methyl]heptylamino][(2,4,6-trimethylphenyl)amino]methylene]-2,4(3H,5H)-furandione;

3-[[heptyl[(4-hexylphenyl)methyl]amino][[4-(trifluoromethyl)phenyl]amino]methylene]-2,4(3H,5H)-furandione;

3-[[[[4-(1,1-dimethylethyl)phenyl]methyl]((Z)-9-octadecenyl)amino][(4-fluorophenyl)amino]methylene]-2,4(3H,5H)-furandione; and 3-[[[4-(dimethylamino)-2,6-dimethylphenyl]amino][[4-(1,1-dimethylethyl)phenyl]heptylamino]methylene]-2,4(3H,5H)-furandione;

or a pharmaceutically acceptable salt thereof.

17. A method for inhibiting intracellular cholesterol esterification which comprises administering, orally or parenterally, to a patient in need thereof, an acyl-coenzyme A:cholesterol acyl transferase inhibiting amount of a compound of the formula:

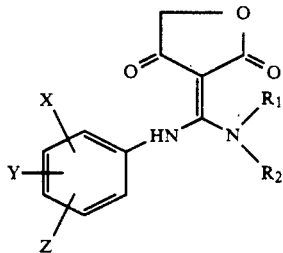

in which
X, Y and Z are, independently, hydrogen, halogen, hydroxy, nitro, cyano, carboxyl, trifluoromethyl, phenyl, amino, alkylamino of 1 to 12 carbon atoms, dialkylamino in which each alkyl group has 1 to 12 carbon atoms, alkyl of 1 to 12 carbon atoms or alkoxy of 1 to 12 carbon atoms;

$R_1$ is alkyl of 1 to 18 carbon atoms, hydroxyalkyl of 1 to 18 carbon atoms, alkenyl of 2 to 18 carbon atoms, cycloalkyl of 5 to 8 carbon atoms, phenyl, benzyl, phenylethyl or substituted phenyl, benzyl or phenylethyl where the substituents are alkyl of 1 to 12 carbon atoms, alkoxy of 1 to 12 carbon atoms, halogen, cyano, trifluoromethyl, amino, alkylamino of 1 to 6 carbon atoms, dialkylamino in which each alkyl group has 1 to 6 carbon atoms, nitro, phenyl, benzyl or phenethyl;

$R_2$ is hydrogen, alkyl of 1 to 18 carbon atoms, cycloalkyl of 5 to 8 carbon atoms, phenyl, benzyl or substituted phenyl or benzyl in which said substituent is alkyl of 1 to 6 carbon atoms, alkoxy of 1 to 6 carbon atoms, halogen, cyano, trifluoromethyl amino, nitro, alkylamino of 1 to 6 carbon atoms or dialkylamino of 1 to 6 carbon atoms;

or a pharmaceutically acceptable salt thereof.

18. A method for inhibiting cholesterol absorption in a patient in need thereof which comprises administering, orally or parenterally, a cholesterol absorption inhibiting amount of a compound of the formula:

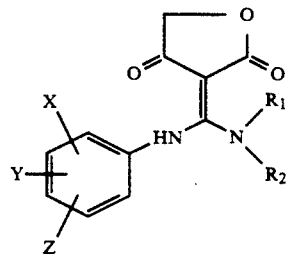

in which
X, Y and Z are, independently, hydrogen, halogen, hydroxy, nitro, cyano, carboxyl, trifluoromethyl, phenyl, amino, alkylamino of 1 to 12 carbon atoms, dialkylamino in which each alkyl group has 1 to 12 carbon atoms, alkyl of 1 to 12 carbon atoms or alkoxy of 1 to 12 carbon atoms;

$R_1$ is alkyl of 1 to 18 carbon atoms, hydroxyalkyl of 1 to 18 carbon atoms, alkenyl of 2 to 18 carbon atoms, cycloalkyl of 5 to 8 carbon atoms, phenyl, benzyl, phenylethyl or substituted phenyl, benzyl or phenylethyl where the substituents are alkyl of 1 to 12 carbon atoms, alkoxy of 1 to 12 carbon atoms, halogen, cyano, trifluoromethyl, amino, alkylamino of 1 to 6 carbon atoms, dialkylamino in which each alkyl group has 1 to 6 carbon atoms, nitro, phenyl, benzyl or phenethyl;

$R_2$ is hydrogen, alkyl of 1 to 18 carbon atoms, cycloalkyl of 5 to 8 carbon atoms, phenyl, benzyl or substituted phenyl or benzyl in which said substituent is alkyl of 1 to 6 carbon atoms, alkoxy of 1 to 6 carbon atoms, halogen, cyano, trifluoromethyl amino, nitro, alkylamino of 1 to 6 carbon atoms or dialkylamino of 1 to 6 carbon atoms;

or a pharmaceutically acceptable salt thereof.

* * * * *